United States Patent
Smart et al.

(10) Patent No.: US 10,238,315 B2
(45) Date of Patent: Mar. 26, 2019

(54) EXHALED BREATH CONDENSATE COLLECTOR

(71) Applicants: Maddison Product Design Limited, Fittleworth (GB); ClearViewIP Limited, Winchester (GB)

(72) Inventors: Nick Smart, Arundel (GB); Andrew Forbes, Fittleworth (GB); Ben Childs, West Grinstead (GB)

(73) Assignees: MADDISON PRODUCT DESIGN LIMITED, Fittleworth, Sussex (GB); CLEARVIEWIP LIMITED, Winchester (GB)

( * ) Notice: Subject to any disclaimer, the term of this patent is extended or adjusted under 35 U.S.C. 154(b) by 259 days.

(21) Appl. No.: 14/908,773

(22) PCT Filed: Jul. 30, 2014

(86) PCT No.: PCT/GB2014/052334
§ 371 (c)(1),
(2) Date: Jan. 29, 2016

(87) PCT Pub. No.: WO2015/015201
PCT Pub. Date: Feb. 5, 2015

(65) Prior Publication Data
US 2016/0166177 A1 Jun. 16, 2016

(30) Foreign Application Priority Data
Aug. 1, 2013 (GB) .................................. 1313817.7

(51) Int. Cl.
*A61B 5/097* (2006.01)
*A61B 5/087* (2006.01)
(Continued)

(52) U.S. Cl.
CPC .............. *A61B 5/097* (2013.01); *A61B 5/082* (2013.01); *A61B 5/087* (2013.01); *A61B 5/095* (2013.01);
(Continued)

(58) Field of Classification Search
CPC ......... A61B 5/097; A61B 5/082; A61B 5/087; A61B 5/095; A61B 10/00;
(Continued)

(56) References Cited

U.S. PATENT DOCUMENTS

2003/0208132 A1 11/2003 Baddour
2007/0173731 A1 7/2007 Meka et al.
(Continued)

FOREIGN PATENT DOCUMENTS

GB 2518953 A 4/2015
WO 1995031721 A1 11/1995
(Continued)

OTHER PUBLICATIONS

PCT Search Report for PCT/GB2014/052334, dated Jul. 30, 2014, 4 pages.
(Continued)

*Primary Examiner* — Navin Natnithithadha
(74) *Attorney, Agent, or Firm* — Rathe Lindenbaum LLP

(57) ABSTRACT

An exhaled breath condensate collection device (10) is described. The device includes a condensation chamber (12) having an inlet and an outlet and arranged such that breath exhaled from the lungs of a user flows through the condensation chamber from the inlet to the outlet; at least one cooling element (16); and a frame (18) supporting the condensation chamber and the at least one cooling element. The frame (18) is movable between a first configuration in which the at least one cooling element is operable to cool the condensation chamber so as to promote the formation of
(Continued)

breath condensate in the condensation chamber, and a second configuration in which the cooling element is displaced from the condensation chamber so as to encourage condensate to flow into a collection region in fluid communication with the condensation chamber. To be accompanied by FIG. 5.

11 Claims, 3 Drawing Sheets

(51) Int. Cl.
    *A61B 5/08*     (2006.01)
    *G01N 33/497*     (2006.01)
    *A61B 10/00*     (2006.01)
    *G01N 1/22*     (2006.01)
    *A61B 5/095*     (2006.01)
    *A61M 16/08*     (2006.01)
    *B01L 3/00*     (2006.01)

(52) U.S. Cl.
    CPC ......... *A61B 10/00* (2013.01); *A61M 16/0808* (2013.01); *B01L 3/5055* (2013.01); *G01N 1/22* (2013.01); *G01N 1/2202* (2013.01); *G01N 33/497* (2013.01); *A61B 2010/0087* (2013.01); *A61B 2560/0443* (2013.01); *A61M 2205/3606* (2013.01); *B01L 2300/1894* (2013.01); *G01N 2001/2244* (2013.01); *G01N 2001/2282* (2013.01)

(58) Field of Classification Search
    CPC ... A61B 2010/0087; A61B 2560/0443; A61M 16/0808; A61M 2205/3606; B01L 3/5055; B01L 2300/1894; G01N 1/22; G01N 1/2202; G01N 33/497; G01N 2010/0087
    USPC .................................................. 600/529–543
    See application file for complete search history.

(56)     References Cited

U.S. PATENT DOCUMENTS

| | | |
|---|---|---|
| 2008/0009761 A1 | 1/2008 | Acker et al. |
| 2008/0214947 A1 | 9/2008 | Hunt et al. |
| 2008/0274014 A1 | 11/2008 | Jumonville et al. |
| 2010/0268106 A1 | 10/2010 | Johnson et al. |
| 2010/0324439 A1 | 12/2010 | Davenport |

FOREIGN PATENT DOCUMENTS

| | | |
|---|---|---|
| WO | 1995033996 A1 | 12/1995 |
| WO | 2004058125 A2 | 7/2004 |
| WO | 2004073497 A2 | 9/2004 |

OTHER PUBLICATIONS

Search Report for GB Application 1413509.9, dated Jan. 28, 2015, 1 page.

EXHALED BREATH CONDENSATE COLLECTOR

FIELD OF THE INVENTION

The present invention relates to a device for collecting exhaled breath condensate (EBC) from the lungs, and particularly but not exclusively to a disposable exhaled breath condensate collector.

BACKGROUND TO THE INVENTION

There are more than 1000 unique substances exhaled in breath and there is a lot of research into mapping the presence and/or ratio of these substances to indicate various disease states. For example, studies have shown that biomarkers in chronic obstructive pulmonary disease (COPD) may be useful in aiding diagnosis and predicting exacerbations, defining specific phenotypes of disease and evaluating the effects of drugs. Other proteomic studies have shown methods which can act as an early detection of cancer based on analysis of exhaled breath condensate (EBC). EBC pH has also been shown to change from normal values in various respiratory diseases. EBC collection may also be useful for rapid detection of infectious processes in the lung, such as tuberculosis (TB), using polymerase chain reaction technology (PCR).

Devices for EBC collection are currently known, but are generally large, expensive to produce and complicated to use. There is thus a need for a cheap, non-invasive, simple, efficient and quick EBC collection apparatus.

SUMMARY OF THE INVENTION

According to a first aspect of the invention, an exhaled breath condensate collection device comprises:
- a condensation chamber having an inlet and an outlet and arranged such that breath exhaled from the lungs of a user flows through the condensation chamber from the inlet to the outlet;
- at least one cooling element; and
- a frame supporting the condensation chamber and the at least one cooling element,
- wherein the frame is movable between a first configuration in which the at least one cooling element is operable to cool the condensation chamber so as to promote the formation of breath condensate in the condensation chamber, and a second configuration in which the cooling element is displaced from the condensation chamber so as to encourage condensate to flow into a collection region in fluid communication with the condensation chamber.

With such a device the cooling element can be rapidly and easily removed from contact with the condensation chamber to allow condensate frozen to the chamber walls to thaw quickly, improving the efficiency of collection.

The frame may comprise at least two leaves, the cooling element being supported by a first leaf and the condensation chamber being supported by a second leaf. The first leaf may be moveable with respect to the second leaf, such that the frame moves between the first configuration and the second configuration. In particular, the first leaf may be hinged to the second leaf, such that the frame hinges between the first configuration and the second configuration. Such a configuration is easy to use and simple to manufacture.

The device may further include a second cooling element. The frame may comprise at least three leaves, the first cooling element being supported by a first leaf, the second cooling element being supported by a third leaf, and the condensation chamber being supported by a second leaf disposed between the first and third leaves. The first and third leaves may be moveable with respect to the second leaf, such that the frame moves between the first configuration and the second configuration. In particular, first and third leaves may be hinged to the second leaf, such that the frame hinges between the first configuration and the second configuration. Such a configuration is advantageous in that the condensation chamber is evenly cooled on both sides.

The cooling element(s) may be removable and may be reusable. The remainder of the device may be formed from low cost materials, and may be disposable. Components not in contact with patient breath, such as the frame, may be formed from recyclable materials, such as cardboard. Cardboard advantageously insulates the user from the cold of the cooling element(s) so the device is comfortable to hold and use, and also serves to stop the user contacting the cooling element(s), so maintaining their low temperature.

The frame may comprise a concertina shape. The frame may comprise a cut-out arranged to support the condensation chamber.

In the second configuration the frame may serve as a stand for the condensation chamber, and may support the condensation chamber in an orientation such that gravity assists the flow of condensate from the condensation chamber into the collection region. Such a configuration simultaneously encourages the thawing of condensate (by removing the cooling elements from contact with the condensation chamber) and promotes the collection of condensate. It also conveniently avoids the need for a user to support the device.

The collection region may be a defined area within the condensation chamber, and/or may be a separate collection chamber.

The frame may be substantially flat and free from protrusions such that a plurality of the claimed devices can be stacked. This enables whole products to be kept in a small volume of a cold storage device, enabling the whole device to be cool from the start and not requiring some patient flow to be wasted while a cold environment within the condensation chamber is created. Further, a large amount of space is available on the outside of the device for printing clear instructions for use.

The device may comprise testing apparatus, such as a lateral flow strip. With such a device test results can be obtained in situ, substantially immediately, without the need to send the collected sample off to a laboratory for analysis. The testing apparatus may be provided in the collection region/chamber, or in a separate test chamber.

The collection region/chamber may be removable. For example, a connector and/or a frangible or weakened area may be provided between the collection region/chamber and the condensation chamber such that the collection region/chamber can be separated (e.g. torn) from the remainder of the device. This simplifies the removal of the collected sample and (if present) the testing apparatus for analysis.

The collection region/chamber and/or condensation chamber may comprise an access port, for example an aperture, which may comprise a cover, though which a sample may be removed from the device. The access port may comprise a frangible portion which can be torn/broken by the user to gain access to the interior of the respective chamber.

The collection region/chamber may comprise a dropper, and may comprise an outlet of a size to stop condensate from dripping out, unless the region/chamber is squeezed by a user.

The device may further comprise a flow meter arranged to give an indication of the rate of flow of exhaled breath through the device. This can provide visual feedback to a healthcare practitioner/patient of the flow rate through the device, and may provide an indication of whether the patient is expelling deep lung or shallow lung breaths.

The flow meter may be in fluid communication with the condensation chamber, and/or may comprise a disc or ball flow meter.

The flow meter may comprise leak holes by which the flow rate through the device may be varied. The leak holes may be provided with covers, which may be removable.

The condensation chamber may be shaped to provide a low resistance to flow, and may be substantially planar with a shallow depth as compared to its width. For example, the condensation chamber may have a depth of less than 10 mm, preferably less than 5 mm. Providing a low resistance to flow through the condensation chamber makes the device easier to use for people with breathing difficulties. Further, providing a condensation chamber with a long, thin form factor aids condensation and collection by promotion droplet formation and accumulation According to a second aspect of the invention there is provided a frame for an exhaled breath condensate collection device, the frame operable to support a condensation chamber and at least one cooling element, wherein the frame is movable between a first configuration in which the at least one cooling element is operable to cool the condensation chamber so as to promote the formation of breath condensate on the walls of the condensation chamber, and a second configuration in which the cooling element is displaced from the condensation chamber so as to encourage the flow of condensate into a collection region in fluid communication with the condensation chamber.

The frame may comprise at least two leaves: a first leaf arranged to support the cooling element, and a second leaf arranged to support the condensation chamber. The first leaf may be hinged to the second leaf, such that the frame hinges between the first configuration and the second configuration.

The frame may additionally comprise a third leaf arranged to support a second cooling element, wherein the second leaf is disposed between the first and third leaves. The first and third leaves may be hinged to the second leaf, such that the frame hinges between the first configuration and the second configuration.

The frame may have any of the further advantageous features described above, with reference to the first aspect of the invention.

According to a third aspect of the invention there is provided an exhaled breath condensate collection device comprising:
- a condensation chamber having an inlet and an outlet and arranged such that breath exhaled from the lungs of a user flows through the condensation chamber from the inlet to the outlet;
- at least one cooling element operable to cool the condensation chamber so as to promote the formation of breath condensate in the condensation chamber; and
- a flow meter arranged to give an indication of the rate of flow of exhaled breath through the device.

Such a device provides a simple and immediate indication of the flow rate through the device, allowing a user to determine whether or not the device is being used correctly. For example, it is possible to determine using such a device whether the expelled breath is a deep or shallow lung breath.

The device may further include any of the further advantageous features described above, with reference to the first aspect of the invention, and may include a frame supporting the condensation chamber, the collection chamber (if present) and the at least one cooling element, wherein the frame is movable between a first configuration in which the at least one cooling element is operable to cool the condensation chamber so as to promote the formation of breath condensate in the condensation chamber, and a second configuration in which the cooling element is displaced from the condensation chamber so as to encourage the flow of condensate from the condensation chamber into the collection chamber.

According to a fourth aspect of the invention there is provided a cooling element for an exhaled breath collection device, the cooling element comprising a water-saturated foam. Such a construction promotes dimensional stability during freezing even if the pack is not frozen in a horizontal position.

BRIEF DESCRIPTION OF THE DRAWINGS

Embodiments of the invention will now be described, by way of example only, with reference to the accompanying drawings in which.

Figure 1:
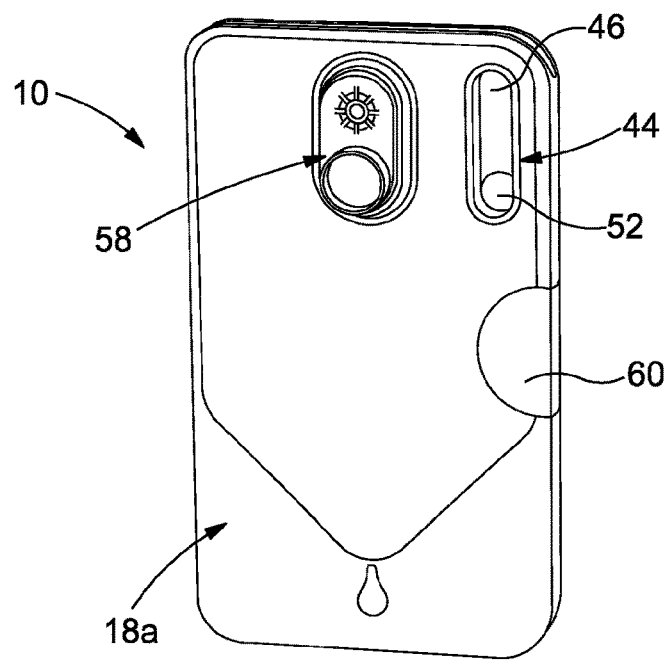
FIG. 1 shows a perspective view of an exhaled breath collection device in a first configuration.
Figure 2:
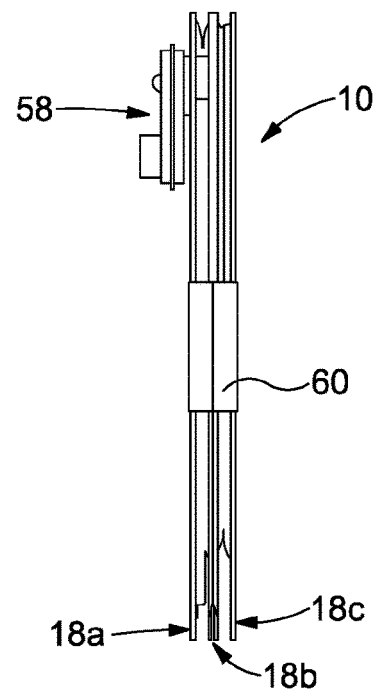
FIG. 2 shows a side view of the device of FIG. 1 in the first configuration.

It will be appreciated that modifications can be made to the example embodiments shown in the drawings without departing from the scope of the claims.

DETAILED DESCRIPTION

An exhaled breath condensate collection device 10 is shown in FIGS. 1, 2, 3 and 5. The device 10 includes a condensation chamber 12, at least one cooling element 16 and a frame 18. The frame 18 serves as a support for the other components (the condensation chamber 12, and the at least one cooling element 16). The frame is movable between a first configuration, shown in FIGS. 1 and 2, and a second configuration, shown in FIG. 3. In the first configuration the at least one cooling element 16 is operable to cool the condensation chamber 12 so as to promote the formation of breath condensate in the condensation chamber, and in the second configuration the cooling element 16 is displaced from the condensation chamber so as to encourage the flow of condensate into a collection region 17 in fluid communication with (and in this case, within) the condensation chamber 12.

The collection region 17 is intended to collect condensate formed in the condensation chamber. To this end the collection region 17 is located in a lower part of the condensation chamber 12 when the device 10 is in a predetermined collection orientation. In the collection orientation (which is the orientation of the device shown in FIGS. 1-3) gravity is able to assist with collection of condensate by encouraging condensate to flow down into the collection region.

Figure 3:
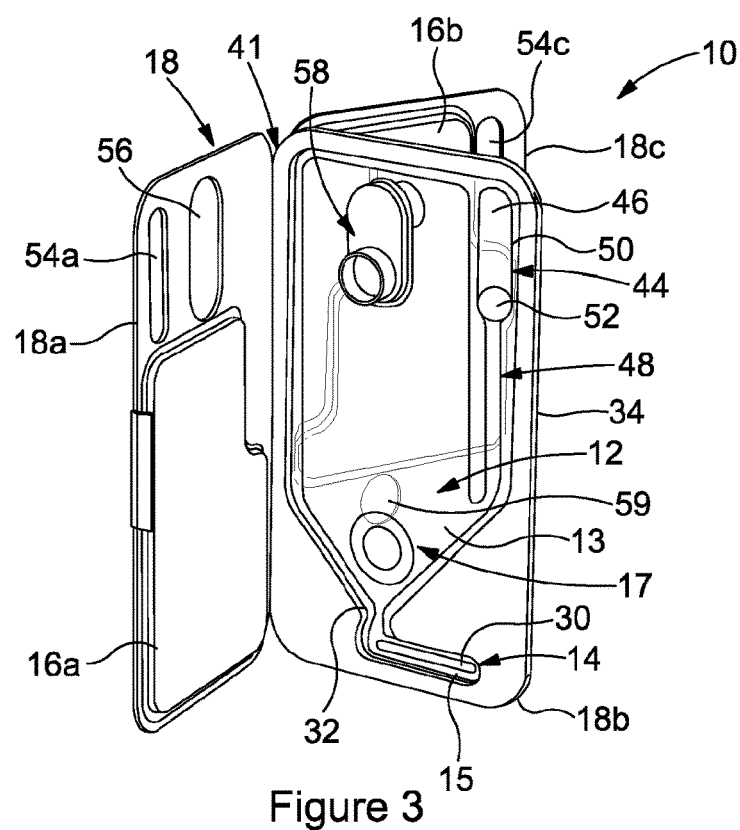
FIG. 3 shows a perspective view of the exhaled breath collection device of FIG. 1 in a second configuration.
Figure 5:
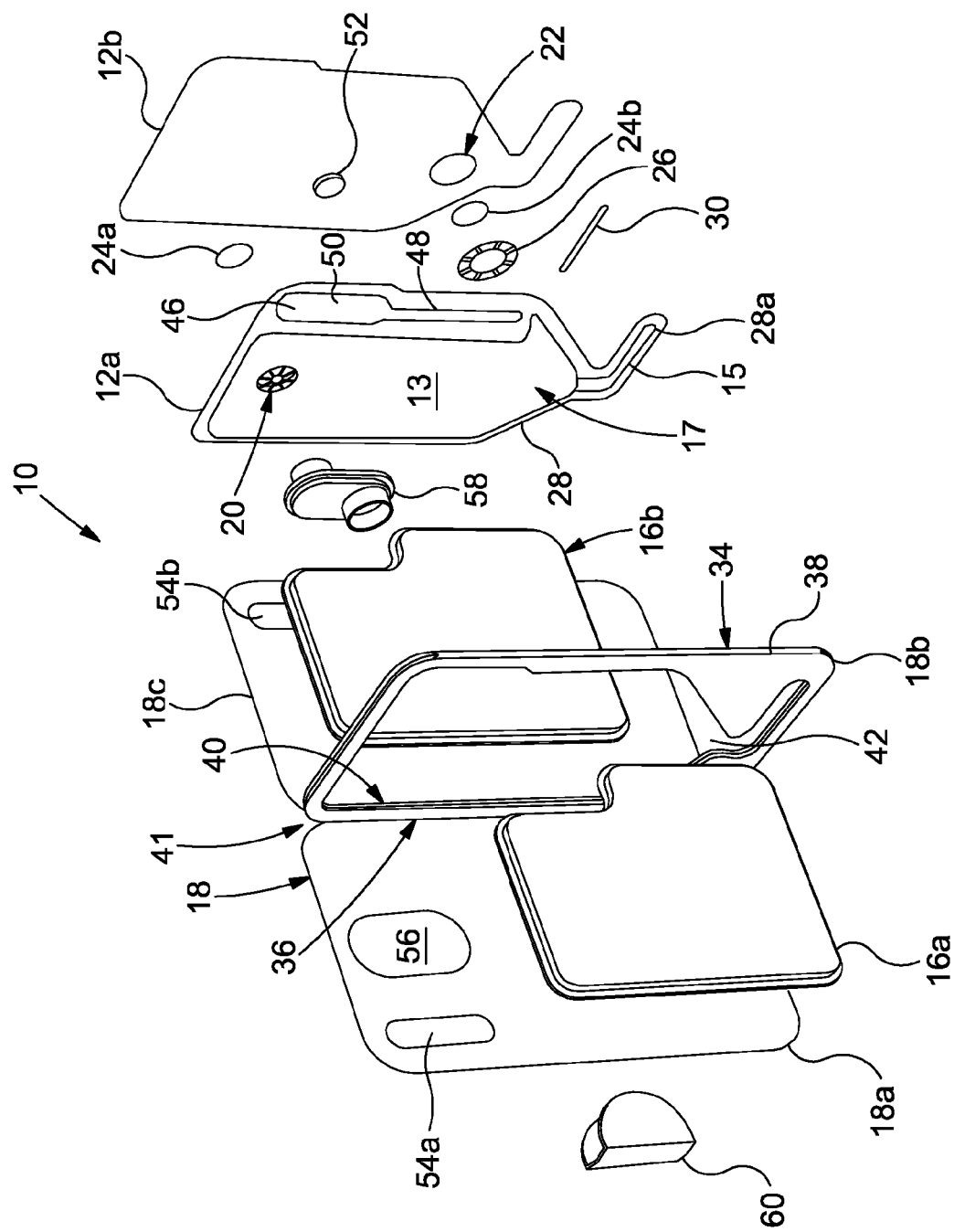
FIG. 5 shows an exploded perspective view of the device of FIG. 1.

The condensation chamber 12, shown best in FIGS. 3 and 5, includes an inlet 20 and an outlet 22. Breath exhaled from the lungs of a user is able to flow through the condensation chamber 12 from the inlet to the outlet.

The condensation chamber 12 includes a cavity 13 within which exhaled breath is able to condense. The cavity 13 is shaped so as to have a large surface area as compared with its volume, to create a large condensation surface. The cavity 13 is also shaped to provide a low resistance to flow. The example cavity shown has a shallow depth as compared with its width, so as to fulfil these criteria. The condensation chamber is substantially planar, and the cavity preferably has a depth of less than 10 mm, for example approximately 5 mm. In contrast, the length and width of the cavity might be in the range 3-20 cm, e.g. 5-15 cm. The device thus has a long and thin form factor which aids condensation and collection by promotion droplet formation and accumulation.

The condensation chamber can be formed from any suitable material. We have found it advantageous to form the condensation chamber from plastic (e.g. thermoform film), as such plastic is simple to obtain, work and dispose of. As shown best in FIG. 5, the chamber 12 is constructed from two pieces which form the walls of the chamber. A first piece 12a forms a first wall of the condensation chamber 12, whilst a second piece 12b forms the second, opposing, wall. The first piece 12a is shaped (e.g. thermoformed) to define features of the condensation chamber. In particular, the first piece includes a ridge 28 which defines a boundary of the cavity 13 within the condensation chamber. The ridge 28 also defines the depth of the cavity.

The second piece 12b of the condensation chamber 12 is a substantially flat film which is sealed at the edges to the first piece 12a so as to close the cavity 13 within.

In the example shown, the first wall of the condensation chamber includes the inlet 20, and the second wall of the chamber includes the outlet 22. Non-return valves are provided to ensure that air is unable to flow through the condensation chamber in the reverse direction (i.e. from outlet 22 to inlet 20). The inlet 20 includes an aperture (in this case, a plurality of apertures arranged in a ring) through which exhaled breath is able to flow. A movable cover 24a is located adjacent the inlet such that the cover can be displaced by airflow in the desired direction through the inlet, but not by airflow in the reverse direction. In the particular example shown the cover 24a is located on the downstream side of the inlet such that the cover 24a can be displaced by airflow through the inlet into the condensation chamber, but air attempting to flow from the chamber in the reverse direction only presses the cover more firmly over the inlet aperture, sealing the cover against the chamber wall.

An alternative non-return valve arrangement is provided at the outlet 22, where a valve insert 26 is proved on the upstream side of the outlet 22, inward of the second wall. The valve insert 26 comprises a plurality of apertures, and a moveable cover 24b is located between the insert 26 and the outlet 22. Both removable covers 24a, 24b are provided with a protrusion or other securing member arranged to be received in a cooperating aperture in the chamber wall (or the valve insert, as the case may be) so as to secure the cover in place. If required, valve insert 26 may be omitted and the moveable cover 24b may be mounted directly to the outlet.

The two pieces 12a and 12b which form the first and second walls of the condensation chamber 12 may also form first and second walls of a further chamber 14. A second ridge 28a formed in the first piece 12a defines a boundary of the condensation chamber. The second ridge 28a touches the first ridge such that when the first and second pieces 12a and 12b are sealed together the further chamber 14 remains in fluid communication with the condensation chamber 12.

In some examples, the further chamber 14 may comprise the collection region 17, and thus may serve as a collection chamber to collect condensate formed in the condensation chamber.

Alternatively or additionally, as in this example, the further chamber 14 may include testing apparatus 30 in the form of a lateral flow strip, and so may serve as a built in test chamber. Thus the collected condensate can be tested for a substance of interest in situ, without the need for the condensate to be transported to a laboratory for analysis. It will be appreciated that the substance of interest is likely to vary depending on the clinical circumstances, and thus the lateral flow strip which is provided and the manner in which it interacts with the condensate can be tailored to meet the needs of the users of the device. For example, condensate may first be arranged to collect in the collection region 17 of the condensation chamber, from where it may be released into the test chamber, for example onto one end of the lateral flow strip, in a controlled manner. A valve may be provided to control the volume and rate of condensate which is released.

It may be that further analysis of the condensate is required, and so in the example shown the further chamber 14 is removable. A weakened area is provided between the further chamber and the condensation chamber such that the chamber 14 can be separated (e.g. torn) from the remainder of the device. The weakened area might include a thinning in the first piece 12a at a defined region 32 between the condensation chamber cavity 13 and the further chamber cavity 15. Alternatively, a connector may be provided in the region 32 between the two cavities, such that they can be separated by a user. The connector may include a seal to prevent condensate from escaping from the separated chamber 14.

The condensation chamber 12 and the further chamber 14 are together supported by the frame 18. The frame 18 also supports at least one cooling element 16, in this case two cooling elements, a first cooling element 16a and a second cooling element 16b.

The frame includes at least two leaves, and in the example shown the frame includes three leaves. A first leaf 18a is arranged to support the first cooling element 16a, and a second leaf 18b is arranged to support the condensation chamber. A third leaf 18c is arranged to support the second cooling element 16b. The second leaf 18b is disposed between the first and third leaves 18a, 18c. The first and third leaves are attached, and in particular hinged, to the second leaf, such that the frame can move (in this case, hinge) between a first configuration, where the cooling elements are adjacent (and in this case touching) the condensation chamber) and a second configuration, where the cooling elements are displaced from the condensation chamber).

The leaves of the frame are essentially planar, and have substantially the same length and width so that they lie neatly on top of each other like the leaves of a book. The outer surfaces of the leaves are substantially flat and free from protrusions, which assists stacking and also provides free space on which instructions for use can be printed.

The frame is constructed from sheet material, in this case corrugated cardboard, which provides good insulation between user and cooling elements so it is comfortable to hold and is minimally heated by patient contact. The example frame shown is made from a single piece of the sheet material folded to form the three leaves. The frame is folded at three locations: a first location 36 between the first and second leaves, a second location 38 at an outer edge 34 of the frame, and a third location 40 between the second and third leaves. The three folds are parallel and the second fold has an opposite sense to the first and third folds, such that the frame has a concertina construction, wherein the first and third leaves are formed from a single thickness of the material and the second (middle) leaf is formed from a double thickness of the material folded back on itself at the outer edge 34 of the frame. When folded, the first and third folds lie substantially on top of and parallel to each other, to form a hinge 41 of the frame.

A cut-out 42 is provided in the two layers making up the second leaf of the frame, and the condensation chamber 12 is supported in the cut-out. The cut-out has substantially the same outline as the two pieces 12a, 12b making up the condensation chamber, such that the chamber 12 fits tightly into the cut-out.

The cooling elements 16a, 16b are supported on the first and third leaves by any suitable means, such as a non-toxic adhesive. Alternatively, the respective cooling elements, or a portion of the cooling elements such as a flange (not shown), may be received in a pocket or slot provided on the respective leaf for that purpose. The cooling elements are constructed so as to promote dimensional stability during freezing, even if the elements are not frozen in a horizontal position. In this example, the cooling elements are filled with a water-saturated foam. However, alternative constructions (e.g. using water filled 'bubble wrap'; or vacuum formed mini-chambers) are possible. The cooling elements are substantially planar, and have a smaller outline than the leaves of the frame so that they do not project beyond the edges of the frame. The cooling elements in the example shown are removable from the frame and can be frozen separately from the remainder of the device if required.

The device further includes a flow meter 44 arranged to give an indication of the rate of flow of exhaled breath through the device. The flow meter is in fluid communication with the condensation chamber, and in this example is a disc flow meter.

In addition to the inlet and outlet holes 20, 22 in the condensation chamber, another smaller outlet hole 46 is situated in one of the walls, in this case the wall formed by the first piece 12a of the condensation chamber. The smaller outlet hole 46 is located within an offshoot air flow channel 48, which is an offshoot of the main air flow path through the device (from the inlet 20 through the condensation chamber 12 to the outlet 22). The offshoot airflow channel 48 is has a width which is small in comparison to the width of the condensation chamber itself (e.g. 1/10th of the width of the condensation chamber or less), so as not to divert too much breath from the main air-flow path through the device. An end portion 50 of the offshoot air flow channel 48 houses an indicator body, in this case an indicator disc 52. In the example shown the end portion 50 is wider than the remainder of the channel 48, so as so allow for the provision a larger and more easily visible disc 52.

The additional outlet hole 46 is located in the end portion of the channel 50, at a location which is distal to the end of the channel which is in communication with the main air flow path. This encourages some of the air flowing through the device to flow along the offshoot channel when the device is in use.

The exact specifications and dimensions of the smaller outlet hole 46, the offshoot air flow channel 48 and the indicator disc 52, can be altered to give a variable resistance to suit patients with different capacities or exhalation rates. Leak-holes can be included which can be opened to allow for variable lung exhalation rates among different patient groups. This rate matching to patients may also be possible using burstable leak-holes. Similarly these could provide safety type valves to avoid bursting the device. In use, the disc 52 rises to a point at which difference in air pressure equals the weight of the disc. By progressively exposing a row of leak holes (between 52 and 46—as shown on FIG. 3), below the disc, this air pressure is reduced, so the balance point will be reached in a graduated manner. There may be a row of holes either side, initially covered with tear strips, so the user can expose one side or the other depending on expected patient lung capacity and the amount of effort required of them. Depending on whether and which leaks holes are exposed, this would give a number of possible flow ranges. This might even be calibrated for a particular flow rate or approximate tidal volume.

The two outer leaves (the first and third leaves 18a and 18c) are provided with matching second and third cut-outs 54a and 54c which are located so as to align with each other and with the end portion 50 of the offshoot air-flow channel 48 so as to provide a flow meter 44 which can be seen from both sides of the device. As breath is expelled into the device the disc rises in the end portion of the channel 48 in proportion to the rate of the flow. This provides a visible indication to the user of the flow through the device. If desired, gradations can be provided on the channel and/or the outer surface of one or both sides of the frame to assist a user in quantifying the flow. The leak holes described above might combine with the graduations for a clearer indication of flow rate.

A fourth cut-out 56 is located in the first leaf 18a of the frame so as to align with the inlet 20 to the condensation chamber. A mouth piece 58 can be passed through the cut-out 56 in the first leaf and connected to the inlet of the condensation chamber so as to permit a patient to breathe into the device. The mouth piece can be substituted by a face mask or similar dependent on the patient condition.

The mouth piece 58 allows for the inhalation of air originating outside the condensation chamber and exhalation of breath into the condensation chamber. This is achieved through the use of 2 oppositely biased (one-way) valves on the mouth piece.

Figure 4:
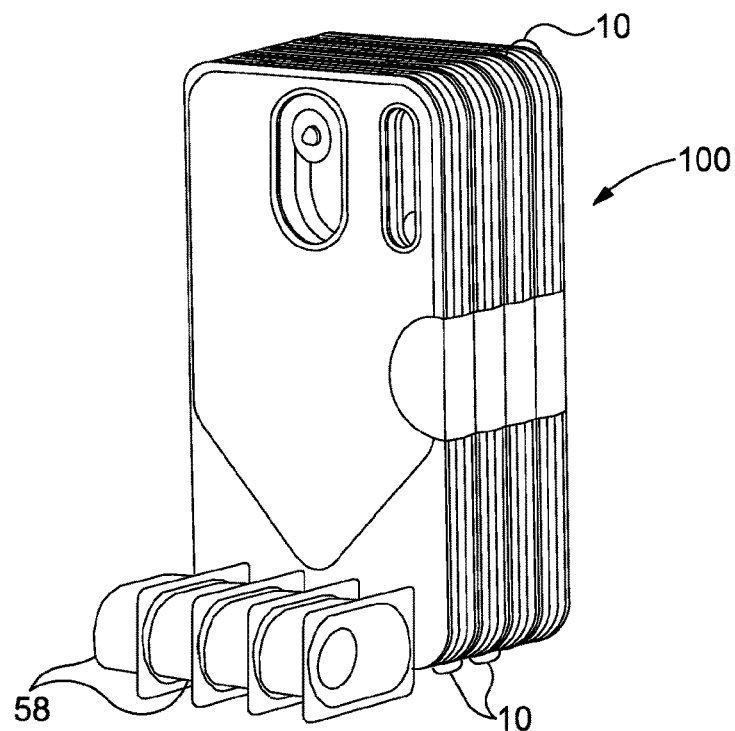
FIG. 4 shows a perspective view of a plurality of stacked exhaled breath collection devices (with stacked externally connectable mouthpieces)

The mouth piece 58 in the example shown is removable, and when removed the device is substantially flat and free of surface protrusions, allowing multiple devices 10 to be stacked together in a stack 100, as shown in FIG. 4. The stack 100 is compact and can be frozen if required.

A perforated label 60 is used to hold the fully constructed device together in the first configuration and allow easy opening into the second configuration after breath testing.

To use the device a user breathes in and out via the mouthpiece. The biased valves within the mouthpiece 58 together with the non-return valves at the inlet 20 and outlet 22 ensure that the users exhaled breath passes through the condensation chamber, whilst inhaled breath is drawn from the external atmosphere. Because the mouthpiece is located in the upper portion of the device, the device extends downwards from the patient's mouth, which makes it easier to hold.

Prior to use the cooling elements of the device at least, or possibly the entire device 10, is chilled to a temperature which will promote the formation of condensate within the condensation chamber. A typical temperature range is 0--30° C. It is noted that a home freezer (typically −18--−30) can be used to cool the device sufficiently if required. Alternatively, if endothermic cooling elements are used then these should be activated. The removable mouth piece (sterile) is also connected to the device if necessary (this step can be omitted if the mouthpiece is integrated within the device.

The patient then breathes in/out through their mouth in communication with the mouth piece, typically for 3-5 minutes (attention not to breathe in/out through nose). The collection time could vary depending on the amount of sample required, and may be pre-specified by a clinician. The patient (and/or their clinician, if present) monitors the position of the flow meter indicator disc to ensure required level of breathing for the amount/type of breath condensate required.

After another time, typically 5 minutes, the clinician/patient breaks the perforated label 60 and opens the device up into the second configuration (shown in FIG. 3). In this configuration the frame acts as a stand for the device, and supports the condensation chamber (and collection chamber, if present) in an orientation in which gravity is able to assist the flow of condensate from the condensation chamber into the collection region. The device is allowed to stand for 5-10 minutes, during which time condensate frozen to the walls of the condensation chamber is able to thaw and collect into the desired location.

As described above, the collection region may contain testing apparatus such as a lateral flow strip. The result of the test can be examined by the clinician or compared to values given in a supporting leaflet or online by the patient. The condensate can be sent for further laboratory analysis if desired.

After use the cooling elements may be refrozen for reuse in another device, and the remainder of the device may be disposed of. The materials not in contact with condensate can be recycled if required. For example, the cardboard outer leaflets of the device can be ripped off and recycled.

It will be understood that the provision of testing apparatus within the collection chamber (or condensation chamber, as may be) is not essential to the invention. In some examples, the device may simply collect condensate for analysis later. The collection region may be a collection chamber which may be removable from the condensation chamber to facilitate off site analysis, as described above with respect to the further chamber 14. Alternatively, the condensation chamber and collection chamber may be unitary, and may be sent for analysis together. If required, the entire device could be sent for analysis.

The collection region has been described herein as being a defined region within the condensation chamber cavity (e.g. a lower region, when the device is in the second configuration). Alternatively, however, the collection region may be a separate cavity to the condensation chamber.

Gases and volatiles may be expressed at the same time as the condensate vapour. These can yield further diagnostic information if captured/scavenged as they pass through the device. This may be achieved by placing materials with capturing properties anywhere on the internal surface, ideally as a patch within the condensation chamber which is easily removable for further testing or also contains indicators that provide a visible test result. A storage vessel could be provided for connection to the device outlet that will retain the gases, if appropriate.

In some examples of the device (including the one shown in the Figures herein) it may be desirable to remove condensate directly from the condensation chamber and/or the collection chamber for analysis. To this end an access port may be provided in the condensation/collection chamber through which a pipette, syringe or other fluid collection apparatus might be inserted into the chamber to draw off some or all of the collected fluid. The access port might be covered or sealed, for example by a tear-off region or a protective label.

The collection chamber/region may be shaped to form a dropper or pipette. In particular, the chamber/region may comprise an outlet of a size to stop condensate from dripping out, unless the chamber/region is squeezed by a user. The chamber/region may then be squeezed by the user when it is desired to extract a sample of EBC from the device.

If desired, the flow meter 44 might be omitted from the device, or alternative forms of flow meter might be provided. In the example described above, the disc within the flow meter might be replaced with any suitable body, such as a ball or ovoid.

It will be appreciated that the device need not be constructed precisely as described herein. Other constructions are possible with the scope of the claims.

For example, the condensation chamber might be formed from one piece rather than two pieces, or may be made from more than two pieces. The components forming the chamber might both be shaped to define features, and in particular, the depth of the chamber. The chamber might be constructed from a material other than thermoform plastic. The skilled man will appreciate that there are many ways of constructing a suitable chamber: for example, two thermo-formed sheets; a bag.

A cheap, non-invasive, simple, lightweight, efficient and quick EBC collection apparatus has been described herein, which is able to make use of current and future tests which analyse disease markers in EBC. Devices for EBC collection which are currently known can be expensive to produce, having complicated valves/airflow paths and requiring the sample to be sent to a laboratory for analysis. The excessive time taken until receiving test results, the requirement of a laboratory to complete the testing process and the high cost of the device itself and the cost of delivering and testing a sample in the laboratory make these devices unsuitable for mass production. Other issues which are inherent in many current EBC devices include: the large amount of space needed for storing several devices, the lack of an indication of flow rate to show efficacy in sample collection, and concern for the impact that disposal of components not in contact with the condensate have on the environment. The devices described herein address these issues, and provide an improved EBC collection device as set out in the claims.

The devices described herein can be manufactured from a small volume of cheap, readily available materials and assembled/shaped using an industrial production line. This imparts a lower price of manufacturing materials and a reduction in clinical waste disposal.

The invention claimed is:

1. An exhaled breath condensate collection device comprising:
   a condensation chamber having an inlet and an outlet and arranged such that breath exhaled from the lungs of a user flows through the condensation chamber from the inlet to the outlet;
   a first cooling element;
   a frame supporting the condensation chamber and the first cooling element; and
   a second cooling element, wherein the frame is movable between a first configuration in which the first cooling element is operable to cool the condensation chamber so as to promote the formation of breath condensate in the condensation chamber, and a second configuration in which the first cooling element is displaced from the condensation chamber so as to encourage condensate to flow into a collection region in fluid communication with the condensation chamber and;

wherein the frame comprises at least three leaves, the first cooling element being supported by a first leaf, the second cooling element being supported by a third leaf, and the condensation chamber being supported by a second leaf disposed between the first and third leaves.

2. The device of claim 1, wherein the first leaf is attached to the second leaf, such that the frame is moveable between the first configuration and the second configuration.

3. The device of claim 1, wherein the frame comprises at least one of:
(i) a concertina shape; and
(ii) a cut-out arranged to support the condensation chamber.

4. The device of claim 1, wherein the frame is at least one of:
(i) formed from a disposable material;
(ii) formed from cardboard; and
(iii) substantially flat and free from protrusions such that a plurality of the claimed devices can be stacked.

5. The device of claim 1, wherein in the second configuration the frame serves as a stand for the condensation chamber, and supports the condensation chamber in an orientation such that gravity assists the flow of condensate from the condensation chamber into the collection region.

6. The device of claim 1, wherein at least one of the collection region and the condensation chamber comprises testing apparatus.

7. The device of claim 1, wherein the collection region is one or more of:
(i) comprised in a collection chamber in fluid communication with the condensation chamber; and
(ii) removable from the condensation chamber.

8. The device of claim 1, further comprising at least one of:
(i) a flow meter arranged to give an indication of the rate of flow of exhaled breath through the device;
(ii) a flow meter in fluid communication with the condensation chamber;
(iii) a disc or ball flow meter; and
(iv) a flow meter comprising leak holes by which the flow rate through the device may be varied.

9. The device of claim 1, wherein the condensation chamber is at least one of:
(i) shaped to provide a low resistance to flow;
(ii) less than 10 mm in depth; and
(iii) less than 5 mm in depth.

10. The device of claim 1, wherein the condensation chamber comprises an access port through which a sample of condensate can be removed by a user.

11. The device of claim 10, wherein the access port comprises an outlet which is sized so as to prevent condensate from passing through the outlet unless the chamber is squeezed by a user.

* * * * *